(12) United States Patent
Do

(10) Patent No.: US 11,369,255 B2
(45) Date of Patent: Jun. 28, 2022

(54) ENDOSCOPE HAVING AN ENDOSCOPE HEAD AND AN ALBARRAN LEVER THAT IS INSERTABLE ON AND DETACHABLE FROM THE ENDOSCOPE HEAD

(71) Applicant: HOYA CORPORATION, Tokyo (JP)

(72) Inventor: Anh Minh Do, Munich (DE)

(73) Assignee: HOYA CORPORATION, Tokyo (JP)

( * ) Notice: Subject to any disclaimer, the term of this patent is extended or adjusted under 35 U.S.C. 154(b) by 273 days.

(21) Appl. No.: 16/328,580

(22) PCT Filed: Jan. 17, 2018

(86) PCT No.: PCT/IB2018/000023
§ 371 (c)(1),
(2) Date: Feb. 26, 2019

(87) PCT Pub. No.: WO2018/185546
PCT Pub. Date: Oct. 11, 2018

(65) Prior Publication Data
US 2020/0178770 A1 Jun. 11, 2020

(30) Foreign Application Priority Data
Jan. 18, 2017 (DE) .......................... 102017100867.5

(51) Int. Cl.
*A61B 1/00* (2006.01)
*A61B 1/018* (2006.01)

(52) U.S. Cl.
CPC ...... *A61B 1/00098* (2013.01); *A61B 1/00101* (2013.01); *A61B 1/018* (2013.01)

(58) Field of Classification Search
CPC .. A61B 1/00098; A61B 1/00101; A61B 1/018
See application file for complete search history.

(56) References Cited

U.S. PATENT DOCUMENTS 5,343,853 A * 9/1994 Komi ................. A61B 1/00098
600/107
5,460,157 A * 10/1995 Prabhu ................. F24C 15/006
126/21 A
(Continued)

FOREIGN PATENT DOCUMENTS

DE 196 27 016 C1 2/1998
DE 102016105028 A1 9/2016
(Continued)

OTHER PUBLICATIONS

U.S. Appl. No. 16/315,422 to Anh Minh Do, filed Jan. 4, 2019.
(Continued)

*Primary Examiner* — Matthew J Kasztejna
(74) *Attorney, Agent, or Firm* — Greenblum & Bernstein, P.L.C.

(57) ABSTRACT

The invention relates to an endoscope having an endoscope head with a working channel for guiding microtools, and an Albarran lever that is insertable on and detachable from the endoscope head, and having a tool guide surface with which a tool that is guidable through the working channel may come into contact in order to be deflected in the lateral direction of the endoscope head. An Albarran lever arrangement space is delimited by two flank sections of the endoscope head that extend in the distal direction. An Albarran lever pivot shaft, from which a shaft section protrudes with respect to the Albarran lever arrangement space with a length, is supported in one of the flank sections. The Albarran lever has a shaft insertion hole for inserting the shaft section, and has a width in a direction that is parallel to the shaft insertion hole.

6 Claims, 7 Drawing Sheets

(56) References Cited

U.S. PATENT DOCUMENTS

| | | | | |
|---|---|---|---|---|
| 5,562,600 | A * | 10/1996 | Matsuno | A61B 1/00098 600/107 |
| 5,674,181 | A * | 10/1997 | Iida | A61B 1/0008 600/127 |
| 5,707,344 | A * | 1/1998 | Nakazawa | A61B 1/0008 600/107 |
| 5,860,913 | A * | 1/1999 | Yamaya | A61B 1/00091 600/127 |
| 5,868,663 | A * | 2/1999 | Katsurada | A61B 1/018 600/107 |
| 6,582,357 | B2 * | 6/2003 | Ouchi | A61B 1/00098 600/107 |
| 6,827,863 | B2 * | 12/2004 | Dolecek | A61M 1/3696 210/787 |
| 7,078,010 | B2 * | 7/2006 | Maki | C01F 7/308 423/625 |
| 7,914,441 | B2 * | 3/2011 | Otawara | A61B 1/018 600/107 |
| 8,066,631 | B2 * | 11/2011 | Wimmer | A61B 1/018 600/107 |
| 2016/0270633 | A1 | 9/2016 | Iwasaka et al. | |
| 2016/0270634 | A1 | 9/2016 | Tanaka et al. | |
| 2016/0270635 | A1 * | 9/2016 | Tanaka | A61B 1/00098 |
| 2016/0270637 | A1 | 9/2016 | Tanaka et al. | |
| 2018/0092512 | A1 * | 4/2018 | Hiraoka | A61B 1/00098 |
| 2018/0249894 | A1 * | 9/2018 | Kolberg | A61B 1/00177 |
| 2019/0298156 | A1 * | 10/2019 | Yamaya | A61B 1/00091 |

FOREIGN PATENT DOCUMENTS

| | | |
|---|---|---|
| DE | 102016105032 A1 | 9/2016 |
| DE | 102016105034 A1 | 9/2016 |
| DE | 102016105035 A1 | 9/2016 |

OTHER PUBLICATIONS

International Search Report issued in International Bureau of WIPO Patent Application No. PCT/IB2018/000023, dated Apr. 30, 2018.

Office Action issued in China Counterpart Patent Appl. No. 201880002885.5, dated Mar. 15, 2021, together with an English translation.

Office Action issued in China Counterpart Patent Appl. No. 201880002885.5, dated Sep. 10, 2021, together with an English translation.

* cited by examiner

ENDOSCOPE HAVING AN ENDOSCOPE HEAD AND AN ALBARRAN LEVER THAT IS INSERTABLE ON AND DETACHABLE FROM THE ENDOSCOPE HEAD

The present invention relates to an endoscope having an endoscope head with a working channel for guiding microtools, and an Albarran lever that is insertable on and detachable from the endoscope head, and having a tool guide surface with which a tool that is guidable through the working channel may come into contact in order to be deflected in the lateral direction of the endoscope head.

Such an Albarran lever may be used in an endoscope for examining, for example, the esophagus as well as the duodenum, the bile duct, the gall bladder, the pancreatic duct, the pancreas, etc.

Such an endoscope has an optical system (illumination device and camera). At the outlet of the working channel, the endoscope also has the Albarran lever, which by pivoting allows a targeted deflection of the tools that are inserted through the working channel.

The endoscope undergoes treatment after use in order to reliably exclude the transmission of all pathogens or microorganisms such as bacteria, viruses, fungi, worms, and spores. During the treatment, the endoscope is initially manually cleaned to completely remove organic material or chemical residues. Machine disinfection or sterilization takes place after the cleaning. The intent is to prevent pathogens or microorganisms, etc., which have come into contact with the endoscope during use thereof, from being transmitted to the patient during the next use.

For example, DE 196 27 016 C1 discloses an endoscope having an Albarran lever. More precisely, the endoscope has a carrier, detachable from the endoscope, in which the Albarran lever is pivotably situated on an axis supported in the carrier. The pivoting of the Albarran lever takes place via a traction cable that is anchored on the Albarran lever and guided in the endoscope.

The object of the present invention is to provide an endoscope in which pathogens that have come into contact with an endoscope are better prevented from being transmitted to the patient during the next use.

This object is achieved by an endoscope having the features of Claim 1. Advantageous refinements are the subject matter of the dependent claims.

The endoscope according to the invention has an endoscope head with a working channel for guiding microtools, and an Albarran lever that is insertable on and detachable from the endoscope head, and having a tool guide surface with which a tool that is guidable through the working channel may come into contact in order to be deflected in the lateral direction of the endoscope head. An Albarran lever arrangement space is delimited by two flank sections of the endoscope head that extend in the distal direction. An Albarran lever pivot shaft, from which a shaft section protrudes with respect to the Albarran lever arrangement space with a length X, is supported in one of the flank sections. The Albarran lever has a shaft insertion hole for inserting the shaft section, and has a width a in a direction that is parallel to the shaft insertion hole, and that is less than the width of the Albarran lever arrangement space, only by a dimension of a movement gap, in a direction parallel to the shaft section, the movement gap being a gap that prevents the Albarran lever from rubbing against the flank sections while pivoting in the Albarran lever arrangement space.

Such an endoscope has a design in which the Albarran lever may be pivoted in the Albarran lever arrangement space in an operationally reliable manner, wherein the Albarran lever itself may be easily installed on and removed from the endoscope. The Albarran lever may thus be designed as a single-use part. The Albarran lever is discarded after use. The next use of the endoscope takes place with a new (fresh) Albarran lever. Transmission of pathogens via an Albarran lever, which may have undercuts and a complex shape, is thus no longer possible.

The Albarran lever may have a proximal base section in which the shaft insertion hole is formed. The base section may have a width b in a direction that is parallel to the shaft insertion hole and that corresponds to the width a minus the length X. This allows the Albarran lever to be easily inserted into the Albarran lever arrangement space, without the need for fastening elements for fastening the Albarran lever to the endoscope. The endoscope is thus less expensive. The shaft section protruding into the Albarran lever arrangement space thus has a simple shape that has no undercuts, etc., to allow engagement or insertion of fastening elements. The shaft section thus also provides fewer options for pathogens to adhere, and may be cleaned more easily and effectively.

The movement gap may have a range of approximately 0.01 mm to $3/10$ mm between the Albarran lever and the particular flank section. The movement gap may preferably have a range of approximately $1/10$ mm to $2/10$ mm between the Albarran lever and the particular flank section. The Albarran lever may thus be securely guided in the Albarran lever arrangement space between the flank sections.

A cap is mountable on the outer circumference, on the distal end section of the endoscope head; in the mounted state the proximal end of the cap is proximal from the Albarran lever arrangement space. The cap closes the still open sides of the Albarran lever arrangement space and prevents the Albarran lever from accidentally sliding out.

The cap may have a lateral tool opening on the side of the tool guide surface, and may be closed on the distal side. The cap thus does not prevent advancement of a tool toward the lateral side.

The aspects of the present invention discussed above may be suitably combined.

The present invention is described in greater detail below with reference to the drawings, based on exemplary embodiments.

EXEMPLARY EMBODIMENT

One exemplary embodiment of the present invention is described below with reference to FIGS. 1 through 10.

The endoscope according to the invention has an endoscope head 1.

The endoscope head 1 is described first, with reference to the figures.

The endoscope head 1 according to the invention is designed as a cylindrical body, and has a working channel 11 and a traction cable channel, not shown, that each extend along the longitudinal direction of the endoscope head 1 and parallel to one another. The traction cable channel guides a traction cable 4 for actuating an Albarran lever 2. The working channel 11 guides microtools for examining, for example, the esophagus as well as the duodenum, the bile duct, the gall bladder, the pancreatic duct, the pancreas, etc.

Figure 1:
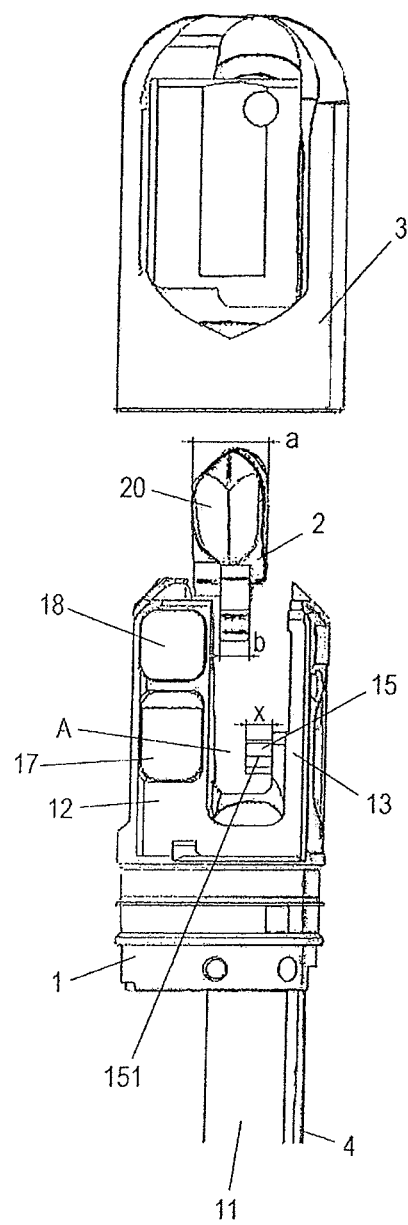
FIG. 1 shows a schematic top view of an endoscope head with an Albarran lever in one exemplary embodiment of the present invention, with the Albarran lever detached.

On the distal side, the endoscope head 1 has an optical system extension 12 on which a camera 17 and an illumination device 18 are provided in a known manner; in FIG. 1 this optical system extension 12 is shown on the left side in the top view. The optical system extension 12 forms a flank section having a camera and illumination. In other words, the optical system extension 12 forms a housing projection having the camera and illumination. This housing projection is situated to the side of an Albarran lever arrangement space A, described below, in order to satisfactorily have the position and the manipulation movements of the microtool in the visual field of the camera.

The working channel 11 ends in a section of the endoscope head 1 that is spaced apart from the distal end, where it forms a distal outlet opening of the working channel.

The Albarran lever 2, which can pivot relative to the endoscope head 1, is situated distal from the distal outlet of the working channel 11. The working channel 11 thus extends in the distal direction toward the Albarran lever 2.

On the distal side, the endoscope head 1 has an Albarran lever support extension 13, shown in FIG. 1 on the right side in the top view. A pivot shaft 15 is supported on the Albarran lever support extension 13 in such a way that it protrudes with respect to an inner space between the optical system extension 12 and the Albarran lever support extension 13. The pivot shaft 15 forms a force transmission section that applies a rotational motion force to the Albarran lever 2. The pivot shaft 15 is the rotary shaft of the Albarran lever 2, in a manner of speaking. The Albarran lever support extension 13 thus forms a flank section having an Albarran lever pivot shaft. In other words, the Albarran lever support extension 13 forms a housing projection having the Albarran lever pivot shaft.

More precisely, the rotational motion force for the Albarran lever 2 is applied by the traction cable 4, whose traction cable nipple is coupled to one end of a lever element 9. The other end of the lever element 9 is connected in one piece to the end of the pivot shaft 15 that is supported in the Albarran lever support extension 13. The opposite end of the pivot shaft 15 forms a shaft section 151 that protrudes from the Albarran lever support extension 13 toward the optical system extension 12.

The Albarran lever 2 is mounted on this shaft section 151 of the pivot shaft 15 protruding into the inner space between the optical system extension 12 and the Albarran lever support extension 13. The shaft section 151 is positioned in such a way that it is opposite from the distal outlet opening of the working channel 11. The inner space between the optical system extension 12 and the Albarran lever support extension 13 forms an Albarran lever arrangement space A. The Albarran lever arrangement space A is thus delimited by the two flank sections 12 and 13 of the endoscope head 1 extending in the distal direction.

The pivot shaft 15 thus has one end that is situated inside the Albarran lever support extension 13. The traction cable 4 engages over the lever element 9 on the end of the pivot shaft 15 opposite from the shaft section 151. In other words, the distal end of the traction cable 4 is in operative connection with the end of the pivot shaft 15 opposite from the shaft section 151. Pulling the traction cable 4 in the proximal direction thus causes the pivot shaft 15 to rotate.

The end of the pivot shaft 15 opposite from the shaft section 151 is sealed off from the surroundings. The traction cable 4 is situated in the traction cable channel. The traction cable channel is likewise sealed off from the surroundings. The traction cable 4 thus has no contact with the surroundings of the endoscope head 1. A sealed space in which the distal end of the traction cable 4, the lever element 9, and the end of the pivot shaft 15 opposite from the shaft section 151 are situated is provided in the Albarran lever support extension 13. This sealed space is open only at the proximal side, via the traction cable channel.

The shaft section 151 of the pivot shaft 15 has the shape of a straight prism with a polygon as the base surface in the longitudinal direction of the pivot shaft 15. A triangle or quadrangle, for example, may be selected as the shape of the shaft section 151. In the present exemplary embodiment, the shaft section 151 has the cross-sectional shape of a quadrangle. The shaft section 151 of the pivot shaft 15 protrudes into the Albarran lever arrangement space A by a dimension X. In other words, the shaft section 151 has a length X (see FIG. 1).

The Albarran lever 2 is described below.

Figure 2:
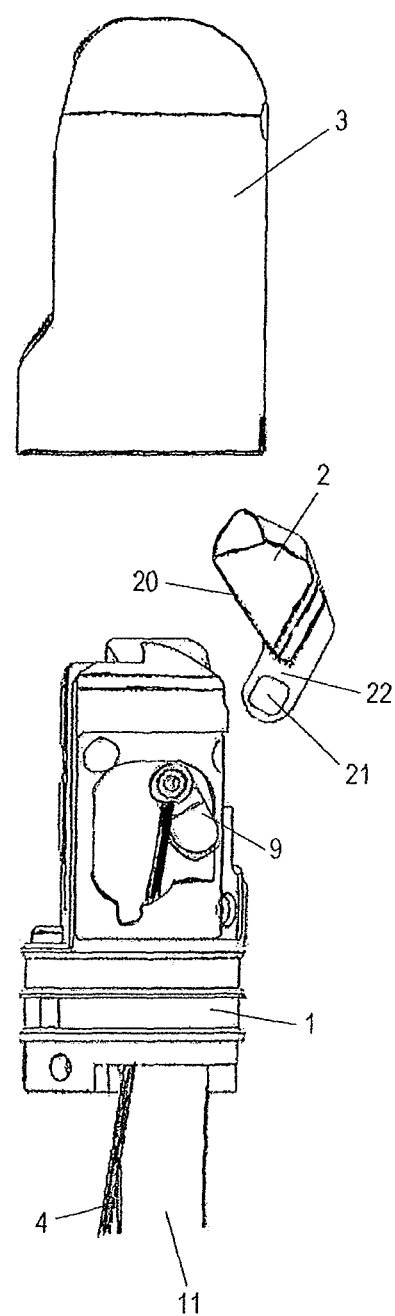
FIG. 2 shows a schematic side view of the endoscope head from FIG. 1.
Figure 3:
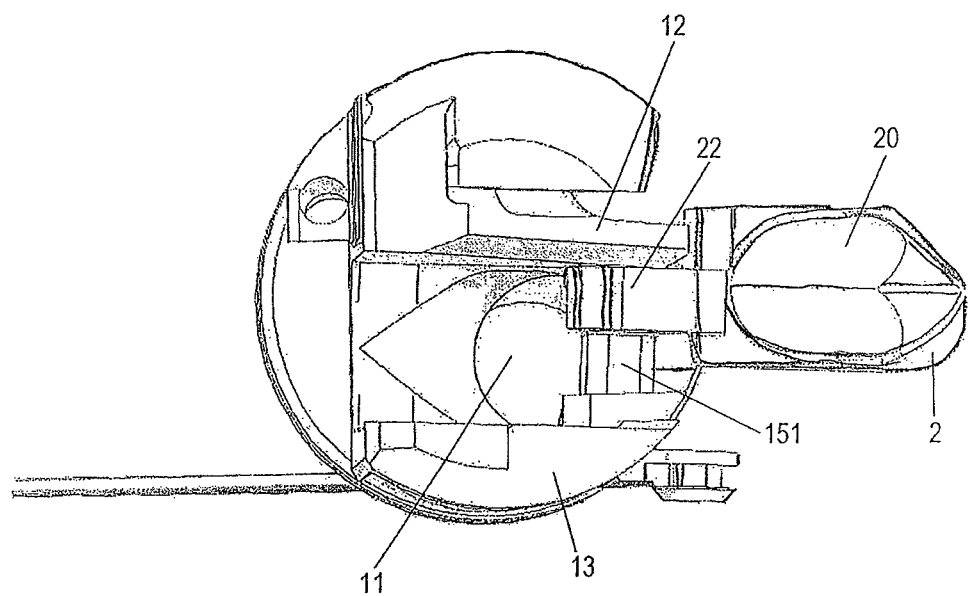
FIG. 3 shows a schematic view of the endoscope head with the Albarran lever from FIG. 1 from the distal side, with the Albarran lever about to be installed.
Figure 4:
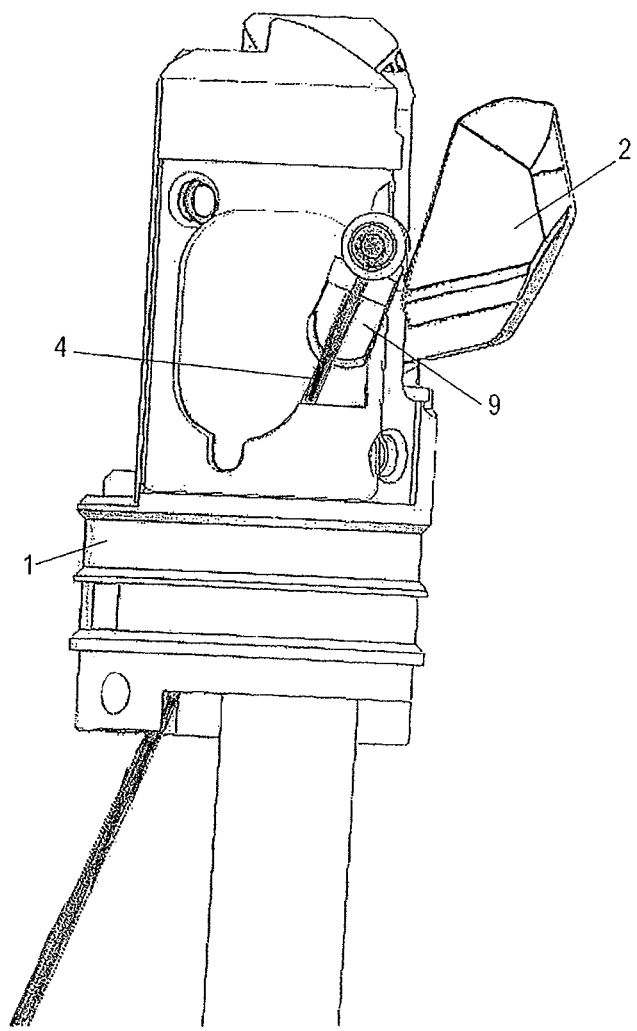
FIG. 4 shows a schematic side view of the endoscope head in the situation from FIG. 3.

The Albarran lever 2 is shown from above in FIG. 1, and the Albarran lever 2 is shown from the side in FIG. 2.

The Albarran lever 2 has a tool guide surface 20 with which a tool that is guidable through the working channel 11 of the endoscope head 1 may come into contact in order to be deflected in the lateral direction of the endoscope head 1 (toward the observer in FIG. 1), so that the tool may be inserted into a bile duct, for example. When the Albarran lever 2 is installed on the endoscope head 1, the tool guide surface 20 is situated opposite from the distal end opening of the working channel 11.

The Albarran lever 2 has a base section 22 on the proximal side. In the installed position of the Albarran lever 2, the base section 22 extends in the proximal direction. The base section 22 has a width of dimension b (see FIG. 1). In the installed position of the Albarran lever 2, the width of the base section 22 extends parallel to the Albarran lever pivot shaft 15.

A shaft insertion hole 21 is designed as a through hole in the proximal area of the base section 22. The shaft insertion hole 21 passes through the base section 22 in a direction perpendicular to the extension direction of the base section 22, as is apparent from FIG. 1. The width b of the base section 22 thus corresponds to the length of the shaft insertion hole 21.

When the Albarran lever 2 is mounted on the endoscope head 1, the shaft insertion hole 21 is placed on the shaft section 151. The shaft insertion hole 21 therefore has an inner shape that forms a countershape to the shape of the shaft section 151.

The shape of the shaft insertion hole 21 must allow a rotation of the pivot shaft 15 to be transmitted to the Albarran lever 2. In the present exemplary embodiment, the shaft insertion hole 21 has a quadrangular shape, as shown in FIG. 2.

On the distal side, i.e., in the area of the tool guide surface 20, or stated differently, in the area without the base section 22, the Albarran lever 2 has two parallel side faces. In the installed position of the Albarran lever 2, these parallel side faces extend in the longitudinal direction of the endoscope. The Albarran lever 2 has a width of dimension a in this distal area. In other words, the parallel side faces in the distal area of the Albarran lever 2 are spaced apart by the dimension a.

In the present invention, the dimension a corresponds approximately to the dimension b+the dimension X.

In addition, the dimension a is selected in such a way that the Albarran lever 2 is rotatable in the Albarran lever arrangement space A with slight play. The width of the Albarran lever arrangement space A, measured parallel to the extension of the pivot shaft 15, is slightly greater than the dimension a. Thus, when the Albarran lever 2 is installed, a very small gap results between the particular side face in the distal area of the Albarran lever 2 and the oppositely situated delimiting face of the Albarran lever arrangement space A, or stated differently, the inwardly pointing (with respect to the Albarran lever arrangement space A) surface of the optical system extension 12 and the Albarran lever support extension 13, i.e., of the particular flank section. In the installed position of the Albarran lever 2, a respective movement gap in a range of approximately 0.01 mm to 0.3 mm results between the Albarran lever 2 and the particular flank section 12, 13. This movement gap may preferably be in a range of approximately 0.1 mm to 0.2 mm. This movement gap prevents the Albarran lever 2 from rubbing against the inwardly pointing surfaces of the optical system extension 12 and the Albarran lever support extension 13 while pivoting in the Albarran lever arrangement space A.

The components of the Albarran lever 2 are made of plastic. The Albarran lever 2 may be manufactured from plastic by means of a 3D printer or injection molding, for example. However, the Albarran lever may be manufactured precisely, and yet at low cost, using a 3D printer or injection molding. Other suitable manufacturing methods may be used, provided that they allow precise, cost-effective production.

The endoscope according to the invention also has cap 3 that is mountable on the endoscope head 1. The cap 3 is a cup-shaped body designed as a cylinder that is provided with a base. The cap 3 has an opening on the proximal side, i.e., on the downwardly pointing side in FIG. 1. The cap 3 is placed on the outer circumference of the distal end section of the endoscope head 1 via this opening. The cap 3 has an engagement apparatus with which it can engage with the outer circumference of the distal end section of the endoscope head 1 in order to ensure secure seating of the cap 3 on the endoscope head 1. For example, the engagement apparatus is provided in the shape of a tab, projection, or hook, etc., that is formed in the proximal area of the cap 3 on the inner circumferential surface, and engages with a corresponding counterelement (a groove, etc.) on the outer circumference of the endoscope head 1.

In the mounted state, the proximal end of the cap 3 is proximal from the Albarran lever arrangement space A. The cap 3 is closed on the distal side.

Figures 9, 10:
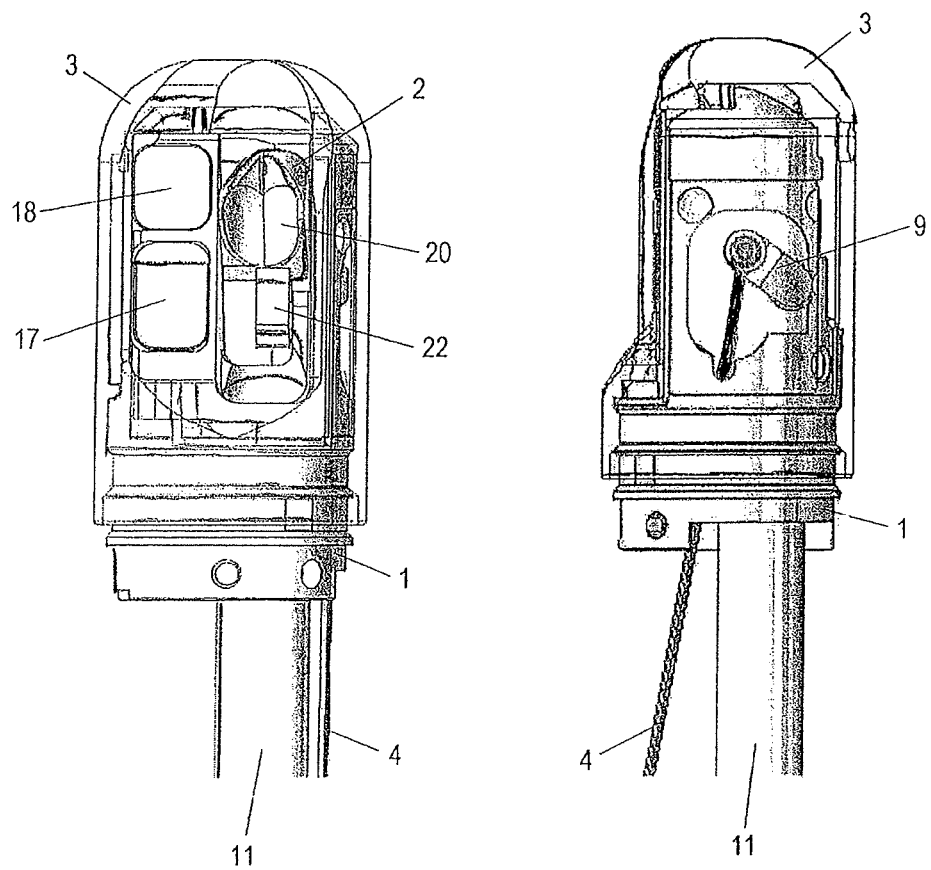
FIG. 9 shows a schematic top view of the endoscope head with the Albarran lever, and the cap mounted.
FIG. 10 shows a schematic side view of the endoscope head from FIG. 9.

The cap 3 has a lateral tool opening on the side of the tool guide surface 20 (see FIG. 9). The lateral tool opening exposes not only the tool guide surface 20, but also at least the camera 17 and the illumination device 18. The lateral tool opening thus allows lateral passage of the tool, illumination by the illumination device 18, and recording of an image by the camera 17.

The cap 3 is likewise made of plastic. The cap 3 may be manufactured from plastic by means of a 3D printer or injection molding, for example. However, the cap 3 may be manufactured precisely, and yet at low cost, using a 3D printer or injection molding. Other suitable manufacturing methods may be used, provided that they allow precise, cost-effective production.

Function of the Invention

The endoscope according to the invention is used as follows.

A new endoscope or a cleaned, sterilized endoscope is provided. This endoscope does not yet have an Albarran lever.

The Albarran lever 2 may be provided as a separate, sterilely packaged module which a user of the endoscope accesses. The user opens the packaging of the Albarran lever 2 and removes the Albarran lever 2.

The structural design of the endoscope head 1 and the Albarran lever 2 is such that the Albarran lever 2 cannot be placed on the shaft section 151 in an installed position, i.e., with the base section 22 pointing in the proximal direction. Although the Albarran lever 2 can be inserted into the Albarran lever arrangement space A with the base section 22 pointing in the proximal direction, the outer circumference of the proximal area of the base section 22 would strike against the outer circumference of the shaft section 151, without the shaft insertion hole 21 being placeable on the shaft section 151. The dimensional relationship between the width of the distal section of the Albarran lever 2 and the width of the Albarran lever arrangement space A does not allow an appreciable oblique position of the Albarran lever 2 in the Albarran lever arrangement space A.

For installation, the Albarran lever 2 must therefore be rotated in such a way that it is approximately perpendicular to the extension direction of the endoscope head 1, with its proximal base section 22 pointing into the Albarran lever arrangement space A. "Perpendicular to the extension direction of the endoscope head 1" means approximately parallel to the direction in which the camera 17 and the illumination device 18 point. In this position of the Albarran lever 2, the base section 22 having the width b may be inserted between the shaft section 151 and the inwardly pointing (with respect to the Albarran lever arrangement space A) surface of the optical system extension 12 (see FIGS. 3 and 4). The base section 22 having the width b fits exactly between the shaft section 151 and the inwardly pointing surface of the optical system extension 12. The traction cable 4 is actuated in such a way that the Albarran lever pivot shaft 15 has the appropriate rotational position.

Figure 5:
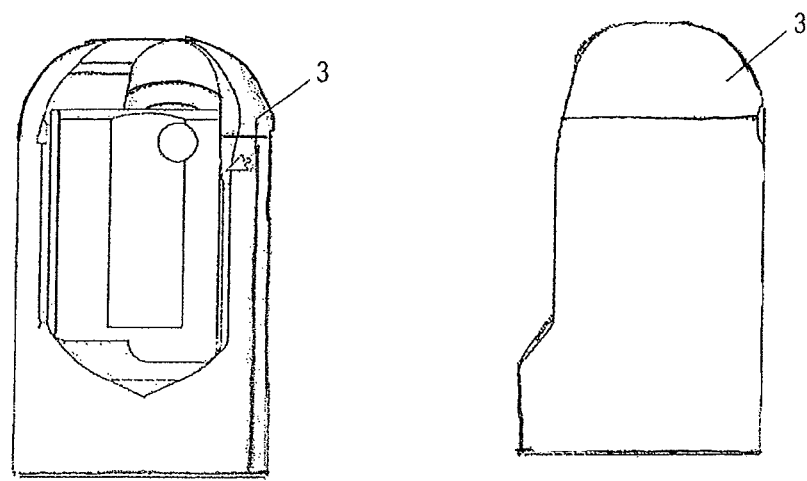
FIG. 5 shows a schematic top view of the endoscope head with the Albarran lever from FIG. 1, with the Albarran lever arranged in the working position.
Figure 6:
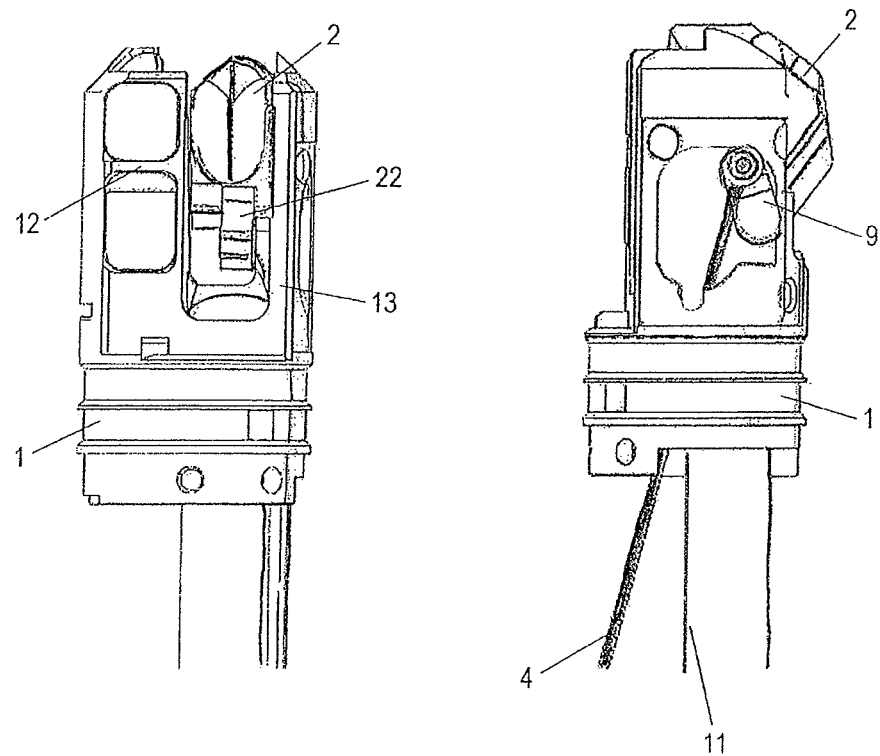
FIG. 6 shows a schematic side view of the endoscope head from FIG. 5.
Figures 7, 8:
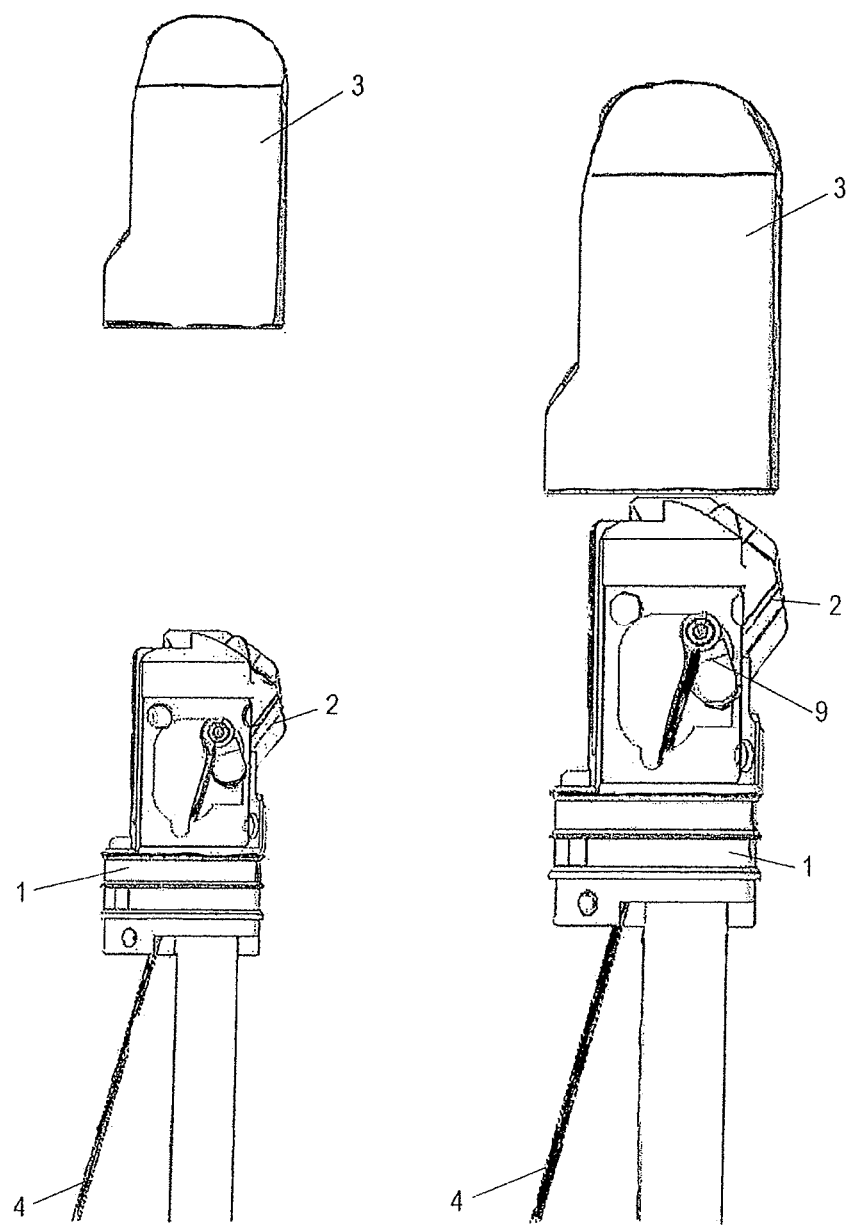
FIG. 7 shows a schematic side view of the endoscope head with the Albarran lever installed.
FIG. 8 shows a schematic side view of the endoscope head with the Albarran lever installed and a cap mounted.

The Albarran lever 2 may now be inserted by laterally moving the base section 22 (downwardly in FIG. 3) in such a way that the shaft section 151 is pushed into the shaft insertion hole 21, and the Albarran lever 2 may then be pivoted into the starting position (see FIG. 5).

The Albarran lever 2 is now pivotable in the Albarran lever arrangement space A. Due to the previously set movement gap, the Albarran lever 2 is guided on the side walls of the Albarran lever arrangement space A, but the Albarran lever 2 does not rub against the side walls of the Albarran lever arrangement space A during pivoting.

The cap 3 is now placed on the outer circumference of the endoscope head 1. The cap 3 thus provides additional security for preventing the Albarran lever 2 from being accidentally removed (sliding out).

Effects of the Invention

The Albarran lever 2 may be provided as a separate, sterilely packaged module which an operator of the endoscope accesses.

The Albarran lever 2 is easily installable on and removable from the endoscope head 1.

The Albarran lever 2 establishes a form-fit connection with the shaft section 151 of the pivot shaft 15, via which the force for pivoting the Albarran lever 2 is reliably transmittable from the endoscope head 1 to the Albarran lever 2.

The invention provides a simple, cost-efficient Albarran lever which is spatially separate from the traction cable 4. Due to its geometric design, an Albarran lever provides many undercuts to which pathogens, etc., may attach during use, and which may possibly remain on the Albarran lever even after intensive cleaning and sterilization. However, the Albarran lever 2 according to the invention may be discarded after a single use. Thus, the Albarran lever 2 according to the invention provides the option for preventing pathogens, etc., which have come into contact with the endoscope during use thereof, from being transmitted to the next patient during the next use.

The traction cable channel is sealed off in the endoscope head, with the traction cable being completely sealed off from the surroundings. The seal of the traction cable channel and of the traction cable is watertight. This prevents pathogens from being able to penetrate into the traction cable channel or come into contact with the traction cable.

The Albarran lever 2 may be used on existing endoscopes that have a corresponding shaft section 151.

Due to the previously set dimensions a, b, X and the width of the Albarran lever arrangement space A, the Albarran lever 2 may be fastened to the endoscope head 1 without auxiliary aids and without fastening means such as screws, etc., but may still be easily removed from the endoscope head 1 after use.

Alternatives

The geometric shape of the shaft section 151 and of the shaft insertion hole 21 is not limited, provided that a form-fit connection between the two is possible.

The engagement of the cap 3 on the outer circumference of the endoscope head 1 is not subject to any limitations. For example, the cap 3 could be screwed onto the outer circumference of the endoscope head 1.

The invention is usable in a duodenoscope. The principle of the invention may also be applied in an ultrasound endoscope and in any other type of endoscope.

A working channel having an Albarran lever at the end of the working channel is shown in the exemplary embodiments. The invention may also be used in endoscopes that have multiple working channels, each with an Albarran lever at the end of the respective working channel.

The described alternatives may be combined, and may be used in all exemplary embodiments.

REFERENCE SIGNS LIST 1 endoscope head
2 Albarran lever
3 cap
4 traction cable
9 lever element
11 working channel
12 flank section with camera and illumination
13 flank section with Albarran lever pivot shaft
15 Albarran lever pivot shaft
17 camera
18 illumination device
20 tool guide surface
21 shaft insertion hole
22 base section
151 shaft section
A Albarran lever arrangement space
X length of the shaft section
a width of the Albarran lever
b width of the base section

The invention claimed is:

1. An endoscope having an endoscope head with a working channel for guiding microtools, and an Albarran lever that is insertable on and detachable from the endoscope head, and having a tool guide surface with which a microtool that is guidable through the working channel may come into contact in order to be deflected in the lateral direction of the endoscope head, wherein an Albarran lever arrangement space is delimited by two flank sections of the endoscope head that extend in the distal direction, wherein an Albarran lever pivot shaft, from which a shaft section partially protrudes into the Albarran lever arrangement space with a protrusion length, is supported in a single one of the flank sections, wherein the Albarran lever has a shaft insertion hole for inserting the shaft section, and has a width in a direction that is parallel to the shaft insertion hole, and that is less than the width of the Albarran lever arrangement space, only by a dimension of a movement gap, in a direction parallel to the shaft section, the movement gap being a gap that prevents the Albarran lever from rubbing against the flank sections while pivoting in the Albarran lever arrangement space, wherein the Albarran lever has a proximal base section in which the shaft insertion hole is formed, and wherein the shaft section extends into the Albarran lever arrangement space by a dimension that is smaller than the half of the width of the Albarran lever arrangement space from one flank section to the other flank section.

2. The endoscope according to claim 1, wherein the movement gap has a range of approximately 0.01 mm to 0.3 mm between the Albarran lever and the respective flank sections.

3. The endoscope according to claim 1, wherein the movement gap has a range of preferably approximately 0.1 mm to 0.2 mm between the Albarran lever and the respective flank sections.

4. The endoscope according to claim 1, having a cap that is mountable on a distal end section of the endoscope head, wherein in the mounted state a proximal end of the cap is proximal from the Albarran lever arrangement space.

5. The endoscope according to claim 4, wherein the cap has a lateral tool opening on a side of the tool guide surface and is closed on a distal side.

6. The endoscope according to claim 1, wherein the proximal base section has a width, in a direction that is parallel to the shaft insertion hole, that is approximately equal to the Albarran lever width in the direction that is parallel to the shaft insertion hole minus the protrusion length of the shaft section with respect to the Albarran lever arrangement space.

* * * * *